US006932814B2

(12) United States Patent
Wood

(10) Patent No.: US 6,932,814 B2
(45) Date of Patent: Aug. 23, 2005

(54) RADIOFREQUENCY PROBES FOR TISSUE TREATMENT AND METHODS OF USE

(75) Inventor: Bradford J. Wood, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/332,297

(22) PCT Filed: Jun. 28, 2001

(86) PCT No.: PCT/US01/20632
§ 371 (c)(1),
(2), (4) Date: Jan. 6, 2003

(87) PCT Pub. No.: WO02/03873
PCT Pub. Date: Jan. 17, 2002

(65) Prior Publication Data
US 2003/0208197 A1 Nov. 6, 2003

Related U.S. Application Data

(60) Provisional application No. 60/217,033, filed on Jul. 10, 2000.

(51) Int. Cl.[7] ................................................ A61B 18/18
(52) U.S. Cl. ........................................ 606/41; 607/101
(58) Field of Search ........................ 606/41, 42, 45–50; 607/98, 99, 113, 116, 101, 102, 128

(56) References Cited

U.S. PATENT DOCUMENTS

| | | |
|---|---|---|
| 4,643,720 A | 2/1987 | Lanciano |
| 5,368,045 A | 11/1994 | Clement et al. |
| 5,728,094 A | 3/1998 | Edwards |
| 5,800,378 A | 9/1998 | Lundquist et al. |
| 5,820,554 A | 10/1998 | Davis et al. |
| 5,827,276 A | 10/1998 | LeVeen et al. |
| 5,849,028 A | 12/1998 | Chen |
| 5,855,576 A | 1/1999 | LeVeen et al. |
| 5,928,163 A | 7/1999 | Roberts et al. |
| 5,935,123 A | 8/1999 | Edwards et al. |
| 6,053,870 A | 4/2000 | Fulton, III |
| 6,071,280 A | 6/2000 | Edwards et al. |
| 6,221,071 B1 | 4/2001 | Sherry et al. |
| 6,450,937 B1 * | 9/2002 | Mercereau et al. ............ 600/7 |
| 6,641,580 B1 * | 11/2003 | Edwards et al. .............. 606/41 |

FOREIGN PATENT DOCUMENTS

| | | |
|---|---|---|
| EP | 0 502 268 | 9/1992 |
| WO | WO 86 05379 | 9/1986 |
| WO | WO 99 37348 | 7/1999 |

OTHER PUBLICATIONS

Hyman, "Radiofrequency Ablation of Unresectable Primary and Metastatic Hepatic Malignancies: Results in 123 Patients," *Dis. Colon Rectum* 43:279 (2000).

(Continued)

*Primary Examiner*—Rosiland Rollins
(74) *Attorney, Agent, or Firm*—Klarquist Sparkman, LLP

(57) ABSTRACT

A device and method for radiofrequency treatment of tissue is disclosed. The device includes an introducer, a plurality of RF electrodes positionable in a nondeployed state within the introducer, and an electrode advancement element. In the nondeployed state, the RF electrodes are contained within the introducer, and separated from the subject's tissue by a plug which substantially occludes the distal end of the introducer. In the method for RF tissue treatment, the introducer is introduced into the tissue of a subject. The RF electrodes are then positioned in the deployed state when the electrode advancement element advances the RF electrodes through the distal end of the introducer, thereby displacing the plug. The electrode advancement element may be a spring-loaded element, and may be actuated by a triggering device on the introducer. The introducer and the RF electrodes may be scored to enhance their visibility in medical imaging studies such as ultrasound, thereby helping to ensure optimal placement of the introducer and the RF electrodes.

31 Claims, 2 Drawing Sheets

OTHER PUBLICATIONS

Man et al., "Radiofrequency Catheter Ablation of Inappropriate Sinus Tachycardia Guided by Activation Mapping," *J. Am. Coll.Cardiol.*35:451–457 (2000).

Powell et al., "Radiofrequency Volumetric Tissue Reduction of the Palate in Subjects with Sleep–Disordered Breathing," *Chest 113*:1163–1174 (1998).

RITA Medical Systems, Inc. advertisement for StarBurst™ XL.

RITA Medical Systems, Inc. advertisement for RITA 1500 System.

RITA Medical Systems, Inc. advertisement for RITA 500 System.

Radio Therapeutics advertisement for Radio Therapeutics Radiofrequency Ablation System (5 pages).

Radio Therapeutics advertisement for Radio Therapeutics RF Ablation System (1 page).

Bilchik et al., *Archives of Surgery 135*:657–664 (2000).

Nelson, et al., *Arch.Otolaryngol.—Head & Neck Surg.126*:736–740 (2000).

* cited by examiner

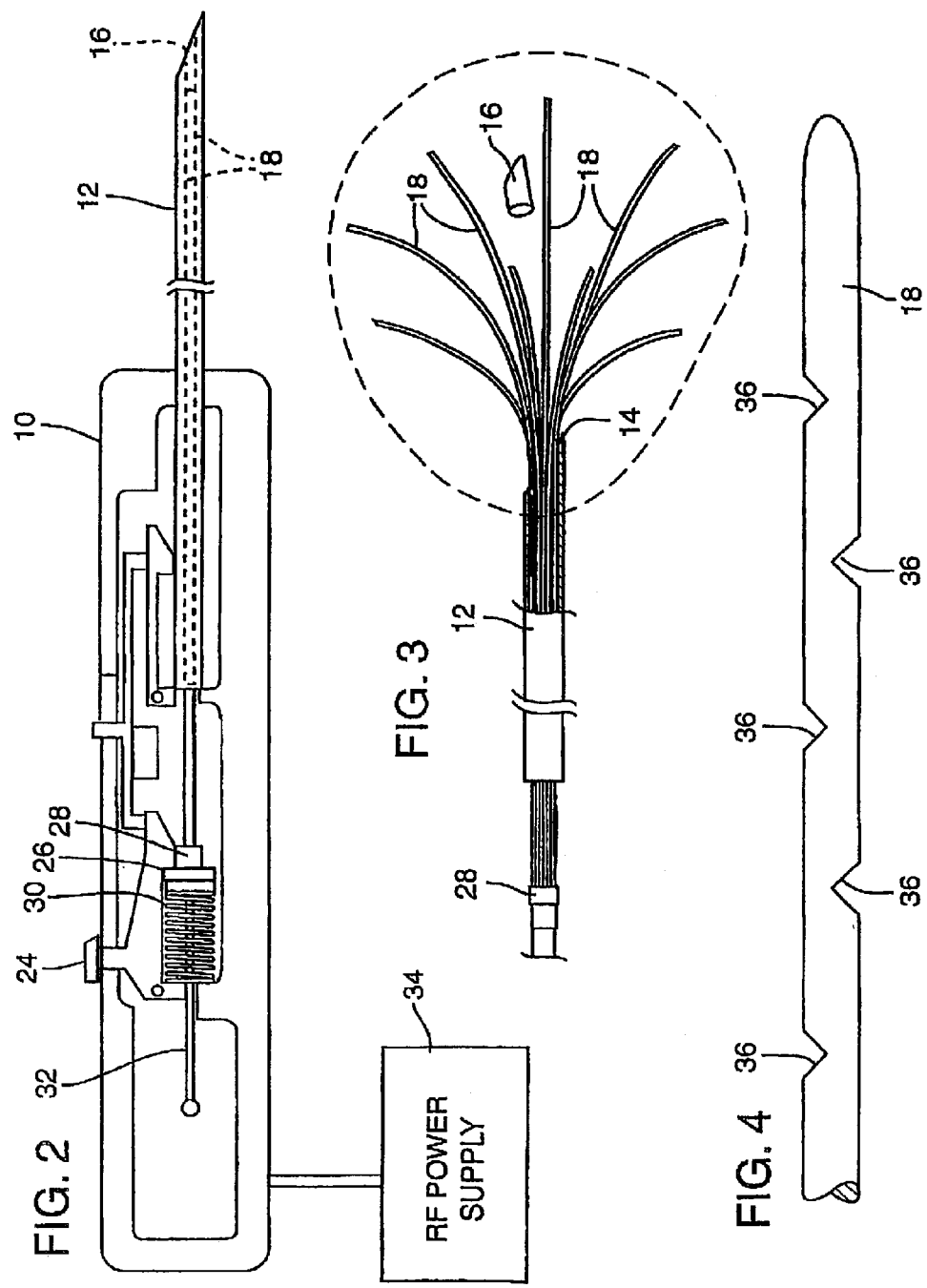

RADIOFREQUENCY PROBES FOR TISSUE TREATMENT AND METHODS OF USE

CROSS REFERENCE TO RELATED APPLICATIONS

This is the U.S. National Stage of International Application No. PCT/US01/20632, filed Jun. 28, 2001, which was published in English under PCT Article 21(2), which in turn claims the benefit of U.S. Provisional Application No. 60/217,033, filed Jul. 10, 2000. Both applications are incorporated herein in their entirety.

FIELD OF THE INVENTION

The present invention relates generally to radiofrequency probes for tissue ablation, and more particularly to improved probes and methods for using such probes in reducing tissue volume.

BACKGROUND OF THE INVENTION

Application of radiofrequency (RF) energy has emerged as an important approach to eliminating or reducing the size of undesirable tissue in a subject. When properly directed and localized, RF energy causes controlled hyperthermia that damages or destroys the undesirable tissue without injuring surrounding tissue. For example, RF energy has been used to treat tumors such as metastatic cancer lesions in the liver, to improve obstructive breathing disorders by increasing airway size, and to eliminate undesirable electrical conduction pathways in the heart. See Hyman, Dis. Colon Rectum 43: 279 (2000); Powell et al., Chest 113: 1163–1174; Man et al., Journal of the American College of Cardiology 35: 451–457 (2000); U.S. Pat. Nos. 5,728,094; and 5,849,028, all of which are herein incorporated by reference in their entirety.

RF energy may be used during minimally invasive procedures. For example, RF electrodes may be placed percutaneously (through the skin) to treat a metastatic cancer lesion in the liver. Such a procedure usually requires only local anesthesia with or without conscious sedation. The target lesion may be localized and appropriate RF electrode placement confirmed by standard medical imaging techniques such as ultrasound. Application of measured amounts of RF energy partially or completely destroys the tumor. Using such minimally invasive procedures, it is often possible to treat a subject and discharge him in the same day. In contrast, an open (full surgical) procedure usually requires general anesthesia and many days to weeks of inpatient recovery.

Recently, RF devices have been developed that may be deployed as an RF electrode array. For example, U.S. Pat. No. 6,071,280, herein incorporated by reference, discloses an array of deployable RF electrodes contained within a delivery catheter. The tip of the delivery catheter is inserted in the tissue, for example percutaneously, and properly positioned near the ablation target. The RF electrodes are manually advanced out of the delivery catheter into the target tissue. On deployment, the RF electrodes fan out into an array that defines the volume of tissue to be ablated by RF energy. Similarly, U.S. Pat. No. 5,827,276, herein incorporated by reference, discloses an RF electrode wire array contained within a delivery catheter. Upon catheter insertion, the RF electrode wires are manually advanced out of the catheter and properly positioned within the target tissue.

SUMMARY OF THE DISCLOSURE

Although these prior uses of RF have undeniable utility, several problems remain. First, there is a significant risk of tissue or vascular injury during placement of the RF electrodes. Usually, this is attributable to a "coring" effect from the open distal end of the delivery catheter (through which the RF electrodes are advanced into the tissue). Such injury may lead to an emergency surgical procedure, or even death of the subject. Second, after RF electrode deployment it is often difficult to precisely determine the location of the probe tips. This may lead to incorrect placement, with inadequate treatment of the target and/or damage to surrounding normal tissue. Third, presently available devices require the operator to manually advance the probe tips from the delivery catheter into the tissue. Thus, the operator is required to use both hands to operate the RF tissue ablation device. In addition, in unusually hard or calcified tissue, it may not be possible for the operator to generate enough force to properly deploy the RF electrodes.

There is a need, therefore, for an RF tissue ablation device that induces minimal tissue trauma, and for which correct placement of the device can be readily ascertained. There is a need for an RF tissue ablation device that is easily operated using only one hand, thereby leaving the operator's other hand free for other uses such as operating a medical imaging device or managing the delivery of radiofrequency energy. There is also need for methods of RF electrode deployment other than manual deployment, so that the RF electrodes may be fully deployed in dense or calcified tissue.

An RF tissue ablation device has been developed to address one or more of these needs. The device has an introducer having a proximal portion and a distal portion, and a plurality of RF electrodes that are positionable in a nondeployed state within the introducer. The RF electrodes are also positionable in the deployed state. The deployed state occurs when an electrode advancement element, operably connected to the RF electrodes, advances the RF electrodes from the introducer into the subject's tissue. In some embodiments, the electrode advancement element includes a spring-loaded element to advance the RF electrodes into the deployed state. The electrode advancement element may be actuated by a triggering device.

In some embodiments, the device has an occluder that substantially occludes the introducer, thereby reducing tissue injury as the device is inserted into a subject. In some embodiments, the occluder is a plug, which may be comprised of a biocompatible material or materials, such as collagen, gelatin, pectin, agar, arabic gum, xanthum gum, tragacanth gum, karaya alginic acid, karaya alginate salts, carrageenan, dextrin, starches, celluloses, polyvinyl alcohol, polyvinylpyrrolidone, polyethylene glycol, and mannans. The occluder may be displaced from the distal end of the introducer as the device transitions from the nondeployed state to the deployed state.

In some embodiments, the device includes surface irregularities which may enhance the device's visibility by medical imaging techniques such as ultrasound. The RF electrodes, the introducer, or both may have surface irregularities.

Also disclosed is a method of ablating tissue in a subject, by inserting an introducer into the subject, deploying a plurality of RF electrodes from the introducer into the subject's tissue, and applying RF energy to the RF electrodes. In certain embodiments of the method, the introducer is substantially occluded by an occluder such as a plug prior to RF electrode deployment. In some embodiments, the plug is a biocompatible material, such as collagen, gelatin, pectin, agar, arabic gum, xanthum gum, tragacanth gum, karaya alginic acid, karaya alginate salts, carrageenan, dextrin, starches, celluloses, polyvinyl alcohol, polyvinylpyrrolidone, polyethylene glycol, and mannans.

In some embodiments of the method, the RF electrodes are deployed by a spring-loaded element, which may be actuated by a triggering device on the introducer. In other embodiments, either the introducer, the RF electrodes, or both may be scored, and their positions may be confirmed by one or more medical imaging methods. The medical imaging methods used to confirm the position of the introducer and/or RF electrodes may be ultrasound, fluoroscopy, computerized tomography, magnetic resonance imaging, or any other suitable medical imaging technique.

BRIEF DESCRIPTION OF THE FIGURES

FIG. 2 is a cross-sectional view of the RF tissue ablation device in its nondeployed state, taken along line 2—2 of FIG. 1.

FIG. 3 shows the distal portion of the RF tissue ablation device, in the device's deployed state.

FIG. 4 illustrates a single RF electrode.

DETAILED DESCRIPTION OF SEVERAL EMBODIMENTS

Figure 1:
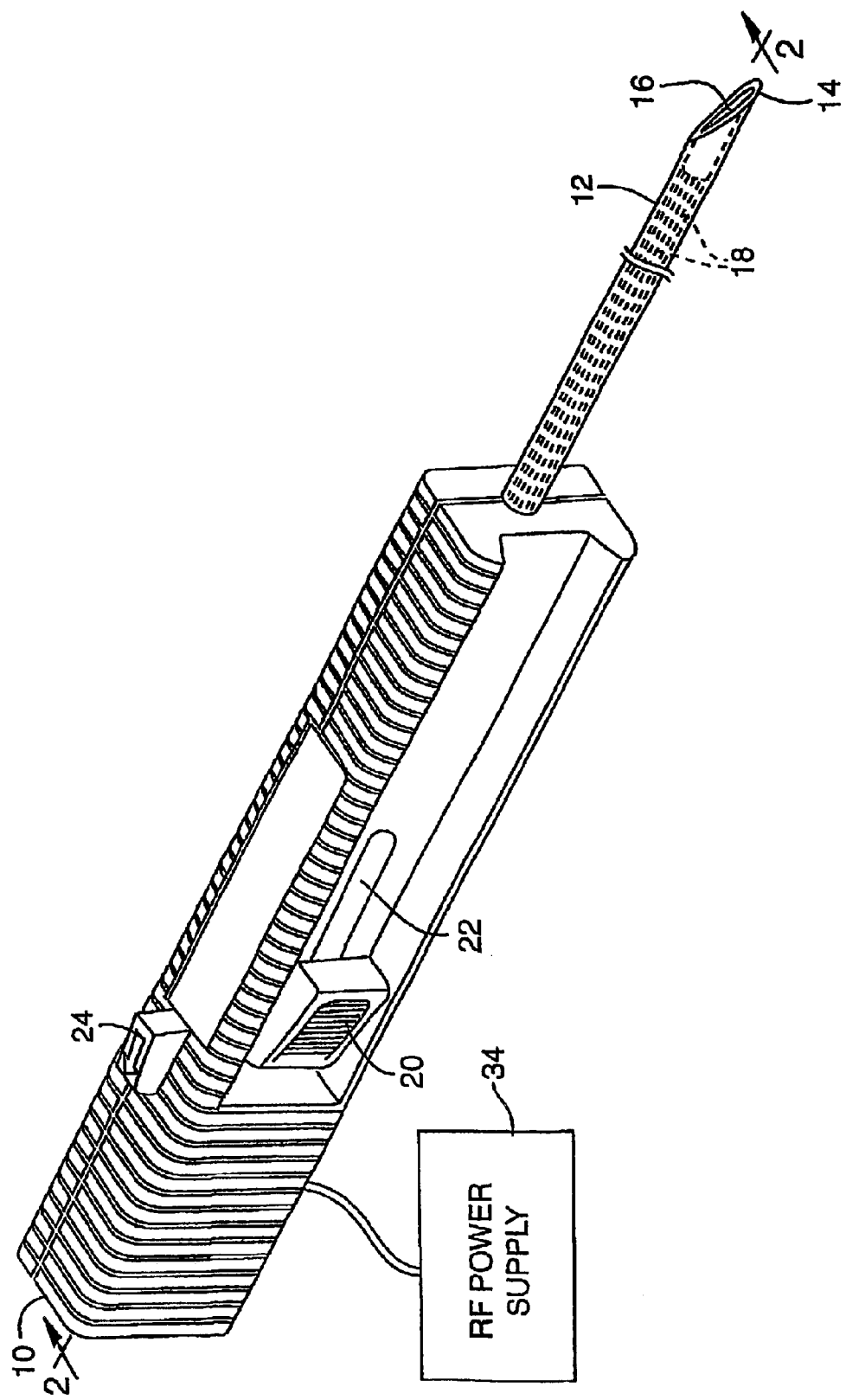
FIG. 1 is a perspective view which illustrates one embodiment of the RF tissue ablation device, showing the device's nondeployed state.

As used herein, proximal refers to a portion of an instrument close to an operator, while distal refers to a portion of the instrument farther away from the operator. As used herein and in the claims, the singular forms "a", "an", and "the" include plural referents unless the context clearly dictates otherwise.

Referring now to the drawings, FIG. 1 illustrates one embodiment of the RF tissue ablation device of the present invention, in the device's nondeployed state. The embodiment consists of a housing 10 and an introducer 12 which protrudes from the distal end of the housing. Introducer 12 is substantially hollow and has a proximal end and a distal end 14. Distal end 14 may be tapered or beveled to a point to enable percutaneous entry of the introducer into the target tissue. Adjacent to distal end 14, and substantially occluding distal end 14, is an occluder 16. The occluder may be a plug, which may be made of any material, especially biocompatible material such as pectin, agar, arabic gum, xanthum gum, tragacanth gum, karaya alginic acid or its salt (e.g., sodium alginate), carrageenan, dextrin, starches (corn starch, rice starch, wheat starch, potato starch, pueraria starch, tapioca starch, carboxymethyl starch, hydroxypropyl starch, hydroxyethyl starch, chemically cross-linked starch, α-starch, and so on), celluloses (hydroxypropylmethyl cellulose, carboxymethyl cellulose, methyl cellulose, methylethyl cellulose, hydroxypropyl cellulose, crystalline cellulose and so on), polyvinyl alcohol, polyvinylpyrrolidone, polyethylene glycol (macrogol), or mannans. A plurality of RF electrodes 18 are contained within the introducer. Slide switch 20 protrudes from the housing and is constrained to move within slot 22. A firing button 24 also protrudes from the housing for deployment of RF electrodes.

FIG. 2 illustrates a cross-section of the embodiment of FIG. 1, through line 2—2. As in FIG. 1, the device's nondeployed state is illustrated. Housing 10 contains proximal end of introducer 12, which protrudes from housing distal end. Introducer's tapered distal end 14 tapers to a point for ease of insertion, and in the illustrated embodiment may be substantially occluded by an occluder 16 such as a plug.

A plurality of RF electrodes 18 are contained within introducer 10. The proximal ends of RF electrodes 18 are attached to electrode advancement element 26, which consists of electrode driver 28 attached to proximal ends of RF electrodes 18, spring 30 attached to electrode driver 28, and firing button 24 attached to proximal end of spring 30 and electrode driver 28, in a manner that maintains spring 30 in compressed position. Slide switch 20 (shown in FIG. 1) is operably connected to electrode driver 28. RF power wires 32 connect to proximal end of RF electrodes 18, pass through center of spring 30, exit housing 10, and connect to RE power supply 34.

In operation, introducer 12 is placed into the subject's tissue. For example, an area of skin overlying the subject's liver or other internal organ may be cleansed with a povidone-iodine solution or other appropriate antiseptic, and anesthetized with a local anesthetic such as 1% lidocaine. The introducer's distal end 14 is inserted through the anesthetized skin to an appropriate depth and location, for example to the approximate site of a primary or metastatic cancer lesion. Typically, the introducer's depth and location is determined with a medical imaging technique, such as ultrasound, magnetic resonance imaging, computerized tomography, fluoroscopy, endoscopy and the like. Once the proper and/or desired introducer position is obtained, RF electrode deployment is then triggered by actuating firing button 24. This releases spring 30 from its compressed position and drives electrode driver 28 forward. RF electrodes 18 are pushed forward by electrode driver 28, thus displacing plug 16 and forcing RF electrodes out distal end 14 of introducer 12. In an alternative embodiment, a stylet may be attached at its proximal end to the electrode driver, and serve the function of driving the occluder out of the introducer. This would relieve mechanical strain on the RF electrode tips that might otherwise occur on impact with the occluder.

Once ejected from introducer 10 by electrode driver 28, RF electrode tips 18 array themselves in the target tissue, and their appropriate position may be confirmed by a medical imaging technique such as ultrasound, magnetic resonance imaging, computerized tomography, fluoroscopy, endoscopy and the like.

RF electrodes may be constructed from a variety of materials including memory metal alloys, as described in U.S. Pat. Nos. 5,935,123 and 6,071,280, which are herein incorporated by reference in their entirety. For some applications, it may be advantageous for the RF electrodes to curve outwards or inwards (evert or invert) as they are deployed, for optimal array formation around the tissue to be ablated or reduced. For such applications, preformed RF electrodes may be used as described in U.S. Pat. Nos. 5,827,276 and 5,855,576, which are herein incorporated by reference in their entirety.

FIG. 3 illustrates the device's deployed state. As in the nondeployed state, introducer 12 contains RF electrodes 18 and electrode driver 28. FIG. 3 illustrates that after deployment, forward displacement of electrode driver 28 ejects plug 16 from distal end 14 of introducer 12, and arrays RF electrodes 18 within the target tissue.

Once the RE tissue ablation device assumes its deployed state, it is usually desirable for the operator or other individual to confirm that the RF electrodes are appropriately situated to accomplish their desired function. This may be accomplished using any appropriate medical imaging technique, such as ultrasound. Occasionally, the operator may desire to redeploy the RF electrodes for better positioning or additional treatment. This may be accomplished by pulling back slide switch 20, for example using the operator's thumb. This compresses spring 30 and causes firing button 24 to catch and lock electrode driver 28, thereby re-establishing the device's nondeployed state as illustrated in FIGS. 1 and 2. The operator may then redeploy the RF electrodes by actuating firing button 24. Those skilled in the art will observe that it is not essential that the RF electrodes be deployed by a spring-loaded mechanism. The RF electrodes may be advantageously deployed manually, for example by positioning the probes using slide switch 20. In general, for such manual positioning, spring 30 would be omitted from the device. Alternatively, the device could include a spring bypass switch that would enable either manual or spring-loaded deployment. In addition, those skilled in the art would recognize that the amount of force and extent of deployment could be readily varied by altering spring characteristics.

For most applications, plug 16 is constructed from biocompatible material such as collagen, gelatin, pectin, agar, arabic gum, xanthum gum, tragacanth gum, karaya alginic acid or its salt (e.g., sodium alginate), carrageenan, dextrin, starches (corn starch, rice starch, wheat starch, potato starch, pueraria starch, tapioca starch, carboxymethyl starch, hydroxypropyl starch, hydroxyethyl starch, chemically cross-linked starch, α-starch, and so on), celluloses (hydroxypropylmethyl cellulose, carboxymethyl cellulose, methyl cellulose, methylethyl cellulose, hydroxypropyl cellulose, crystalline cellulose and so on), polyvinyl alcohol, polyvinylpyrrolidone, polyethylene glycol (macrogol), or mannans. The materials can be used singly or in an appropriate combination. In some applications, it is advantageous for the melting point of the plug material to be sufficiently low such that during device operation, the heat generated by the device melts the plug. Alternatively, the plug may melt, dissolve or otherwise degrade without the need for heat application.

To enhance ultrasonic visibility of RF electrodes, an introducer and/or RF electrodes may be provided with surface irregularities. Such surface irregularities enhance the return of sound waves to an ultrasound transducer, by increasing the amount of surface area appropriately oriented to receive sound waves and reflect them. The surface irregularities may be in virtually any regular or irregular arrangement, may be elevations or depressions in the surface, and may be circumferential or partial. FIG. 4 illustrates one embodiment of an RF electrode with echogenic surface irregularities, namely an indented RF electrode. RF electrode 18 has a series of noncircumferential notches 36 that indent the electrode. The indentations create additional surfaces that increase the amount of ultrasonic reflection and aid in localization of the deployed RF electrodes. Although FIG. 4 illustrates substantial notches, the electrode's surface irregularities may in fact be quite minimal. For example, just a few fine serrations on an electrode will substantially enhance ultrasonic visibility.

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

I claim:

1. A tissue ablation device, comprising:
   an introducer having a proximal portion and a distal portion;
   one or more RF electrodes movable between a nondeployed state within the introducer, and a deployed state in which the electrodes extend from the distal portion of the introducer;
   an electrode advancement element coupled to the RF electrodes and capable of moving the RF electrodes between the nondeployed state and the deployed state; and
   an occluder that occludes the distal portion of the introducer when the electrode device is in the nondeployed state, wherein the occluder comprises a plug of biocompatible material mounted for ejection from the distal portion of the introducer when the electrodes are moved to the deployed state.

2. The tissue ablation device of claim 1, further comprising surface irregularities on the introducer.

3. The tissue ablation device of claim 1, further comprising surface irregularities on one or more RF electrodes.

4. The tissue ablation device of claim 1, wherein the electrode advancement element comprises a spring-loaded element that advances the electrode device from the nondeployed state to the deployed state.

5. The tissue ablation device of claim 4 wherein the spring-loaded element is capable of being actuated by a triggering device on the introducer.

6. The tissue ablation device of claim 1, further comprising a housing configured to enclose a proximal end of the introducer and at least a portion of the electrode advancement element.

7. The tissue ablation device of claim 6, wherein the housing and the electrode advancement element are configured to be operable using a single hand.

8. The tissue ablation device of claim 6, wherein the electrode advancement element comprises a spring-loaded element configured to deploy the electrodes through a distal end of the introducer upon actuation of a firing button, the firing button being positioned on an exterior of the housing.

9. The tissue ablation device of claim 8, further comprising a slide switch coupled to the electrode advancement element and operable to move the RF electrodes to a nondeployed state, thereby compressing the spring-loaded element.

10. The tissue ablation device of claim 1, wherein the occluder is positioned at a distal end of the introducer.

11. The tissue ablation device of claim 10, wherein the occluder and the distal end of the introducer are beveled.

12. The tissue ablation device of claim 1, wherein the occluder comprises a material that melts from heat generated during operation of the tissue ablation device.

13. A tissue ablation device, comprising:
   an introducer having a proximal portion and a distal portion;
   one or more RF electrodes movable between a nondeployed state within the introducer, and a deployed state in which the electrodes extend from the distal portion of the introducer;
   an electrode advancement element coupled to the RF electrodes and capable of moving the RF electrodes between the nondeployed state and the deployed state; and
   an occluder that occludes the distal portion of the introducer when the electrode device is in the nondeployed state, the occluder comprising a plug of biocompatible material, wherein the biocompatible material is selected from the group consisting of: collagen, gelatin, pectin, agar, arabic gum, xanthum gum, tragacanth gum, karaya alginic acid, karaya alginate salts, carrageenan, dextrin, starches, celluloses, polyvinyl alcohol, polyvinylpyrrolidone, polyethylene glycol, and mannans.

14. A method of ablating tissue in a subject, comprising:
inserting an introducer into the subject;
deploying a plurality of RF electrodes from the introducer into the subject's tissue; and
applying RF energy to the RF electrodes;
wherein prior to deployment of the RF electrodes, the introducer's distal end is occluded by an occluder, and the occluder comprises a plug of biocompatible material mounted for ejection from the distal end of the introducer when the electrodes are deployed.

15. The method of claim 14, wherein the introducer has surface irregularities.

16. The method of claim 14, wherein one or more of the RF electrodes has surface irregularities.

17. The method of claim 14, wherein the RF electrodes are deployed by a spring-loaded element.

18. The method of claim 17, wherein the spring-loaded element is capable of being actuated by a triggering device.

19. The method of claim 14, wherein the position of the introducer is confirmed by one or more medical imaging methods.

20. The method of claim 14, wherein the position of one or more RF electrodes is confirmed by one or more medical imaging methods.

21. The method of claim 19 or claim 20, wherein the medical imaging method is selected from the group consisting of ultrasound, fluoroscopy, computerized tomography, endoscopy and magnetic resonance imaging.

22. The method of claim 14, wherein deploying the plurality of RF electrodes ejects the occluder from the distal end of the introducer and into the subject.

23. The method of claim 22, further comprising melting the occluder ejected from the distal end of the introducer with heat generated from the RF energy applied to the RF electrodes.

24. The method of claim 22, wherein inserting the introducer into the subject and deploying the plurality of RF electrodes is performed using a single hand of an operator.

25. The method of claim 14, further comprising:
moving the plurality of RF electrodes back to a nondeployed state; and
repositioning the introducer in the subject.

26. The method of claim 25, wherein the moving and repositioning are performed using a single hand of an operator.

27. A method of ablating tissue in a subject, comprising:
inserting an introducer into the subject;
deploying a plurality of RF electrodes from the introducer into the subject's tissue; and
applying RF energy to the RF electrodes;
wherein prior to deployment of the RF electrodes, the introducer's distal end is occluded by an occluder, the occluder comprising a plug of biocompatible material, wherein the biocompatible material is selected from the group consisting of: collagen, gelatin, pectin, agar, arabic gum, xanthum gum, tragacanth gum, karaya alginic acid, karaya alginate salts, carrageenan, dextrin, starches, celluloses, polyvinyl alcohol, polyvinylpyrrolidone, polyethylene glycol, and mannans.

28. The method of claim 27, wherein the position of the introducer, one or more of the RF electrodes, or both the introducer and the one or more of the RF electrodes is confirmed by one or more medical imaging methods.

29. The method of claim 27, wherein deploying the plurality of RF electrodes ejects the occluder from the distal end of the introducer and into the subject.

30. The method of claim 29, further comprising melting the occluder ejected from the distal end of the introducer with heat generated from the RF energy applied to the RF electrodes.

31. The method of claim 27, wherein inserting the introducer into the subject and deploying the plurality of RF electrodes is performed using a single hand of an operator.

* * * * *